(12) United States Patent
Ji et al.

(10) Patent No.: US 10,156,505 B2
(45) Date of Patent: Dec. 18, 2018

(54) ANALYSIS METHOD OF TENSIONING PROCESS OF FINE MASK PLATE

(71) Applicants: BOE TECHNOLOGY GROUP CO., LTD., Beijing (CN); ORDOS YUANSHENG OPTOELECTRONICS CO., LTD., Ordos, Inner Mongolia (CN)

(72) Inventors: Fengli Ji, Beijing (CN); Minghua Xuan, Beijing (CN); Shanshan Bai, Beijing (CN); Jiantao Liu, Beijing (CN); Jingbo Xu, Beijing (CN)

(73) Assignees: BOE Technology Group Co., Ltd., Beijing (CN); Ordos Yuansheng Optoelectronics Co., Ltd., Ordos, Inner Mongolia (CN)

(*) Notice: Subject to any disclaimer, the term of this patent is extended or adjusted under 35 U.S.C. 154(b) by 379 days.

(21) Appl. No.: 14/778,881

(22) PCT Filed: Jan. 16, 2015

(86) PCT No.: PCT/CN2015/070874
§ 371 (c)(1),
(2) Date: Sep. 21, 2015

(87) PCT Pub. No.: WO2016/050013
PCT Pub. Date: Apr. 7, 2016

(65) Prior Publication Data
US 2016/0238499 A1    Aug. 18, 2016

(30) Foreign Application Priority Data

Sep. 29, 2014 (CN) .......................... 2014 1 0515610

(51) Int. Cl.
*G01L 1/00* (2006.01)
*G01N 3/08* (2006.01)
*G06F 17/50* (2006.01)

(52) U.S. Cl.
CPC ........... *G01N 3/08* (2013.01); *G06F 17/5018* (2013.01); *G01N 2203/0216* (2013.01)

(58) Field of Classification Search
None
See application file for complete search history.

(56) References Cited

U.S. PATENT DOCUMENTS

| | | | |
|---|---|---|---|
| 2003/0081193 A1 | 5/2003 | White et al. | |
| 2005/0115503 A1* | 6/2005 | Hagiwara | C23C 14/042 118/721 |
| 2014/0130735 A1* | 5/2014 | Kim | H01L 51/0011 118/504 |

FOREIGN PATENT DOCUMENTS

| | | |
|---|---|---|
| CN | 1625312 A | 6/2005 |
| CN | 101866378 A | 10/2010 |

(Continued)

OTHER PUBLICATIONS

First Office Action dated Dec. 27, 2016 in corresponding Chinese Application No. 201410515610.5.

(Continued)

*Primary Examiner* — Cory Eskridge
(74) *Attorney, Agent, or Firm* — Nath, Goldberg & Meyer; Joshua B. Goldberg

(57) ABSTRACT

The present invention discloses an analysis method of a tensioning process of a fine mask plate. The analysis method, based on the simulation function of ANSYS software, finds an appropriate tensile force for stretching a fine mask plate and a corresponding actual counterforce applied to a metal frame before each fine mask plate is welded onto the metal frame through establishing a finite element model (Continued)

of the fine mask plate and a finite element model of the metal frame. The analysis process requires no physical tests, thereby effectively avoiding damaging the fine mask plate and further effectively saving the test cost.

7 Claims, 4 Drawing Sheets

(56) References Cited

FOREIGN PATENT DOCUMENTS

| CN | 102169286 A | 8/2011 |
|---|---|---|
| CN | 102737136 A | 10/2012 |
| CN | 103695841 A | 4/2014 |
| CN | 103886126 A | 6/2014 |
| CN | 104281747 A | 1/2015 |
| EP | 1564793 A1 | 8/2005 |
| WO | 2011/085019 A2 | 7/2011 |

OTHER PUBLICATIONS

International Search Report dated Jun. 19, 2015 in corresponding International Application No. PCT/CN2015/070874 along with an English translation of the Written Opinion of the International Searching Authority.

P. Lenius, et al., "Mechanical distortions of support frames for x-ray lithography masks"; Journal of Vacuum Science & Technology B: Microelectronics Processing and Phenomena; vol. 8 No. 6 Nov./Dec. 1990; pp. 1570-1574.

Extended European search report dated Apr. 6, 2018 for corresponding application No. 15791467.2.

* cited by examiner

ANALYSIS METHOD OF TENSIONING PROCESS OF FINE MASK PLATE

FIELD OF THE INVENTION

The present invention relates to the technical field of display, in particular to an analysis method of a tensioning process of a fine mask plate.

BACKGROUND OF THE INVENTION

In manufacturing an electroluminescent light-emitting device, material of each layer in the electroluminescent light-emitting device needs to be evaporated onto an array substrate by an evaporation process. Furthermore, during the evaporation, a corresponding fine mask plate needs to be used.

However, due to the occurrence of high temperature during the evaporation, the fine mask plate will be subject to thermal expansion, thereby resulting in drooping of the fine mask plate due to its gravity and changed geometry of the fine mask plate; and as a further result, the evaporation material cannot be evaporated onto a designated position.

FIG. 1 is a schematic diagram illustrating a case where a plurality of fine mask plates are welded to a metal frame. As shown in FIG. 1, in order to solve the problem described above, in the prior art, a plurality of strip-shaped fine mask plates 2 are welded to one metal frame 1, and then the strip-shaped fine mask plates 2 and the metal frame are used for the evaporation process together. Specifically, the fine mask plates 2 are stretched by an appropriate force first, then an appropriate counterforce is applied to the metal frame 1 to deform the metal frame 1, and finally, the stretched highly fine mask plates 2 are welded onto the frame to which the counterforce has been applied. By using a restoring force resulted from the deformation of the metal frame 1, the fine mask plates 2 are tightened by welding points 3, so that the fine mask plates 2 will not droop during the evaporation.

At present, in order to find an appropriate tensile force for stretching a fine mask plate and a counterforce for deforming the metal frame, physical tests are generally needed. However, during the physical tests, the fine mask plate may be damaged easily due to fine openings and small thickness thereof, and meanwhile, the fine mask plate is high in manufacturing cost, which directly increase the overall cost during the physical tests.

SUMMARY OF THE INVENTION

The preset invention provides an analysis method of a tensioning process of a fine mask plate, in order to solve the technical problem in the prior art that physical tests lead to high cost during the analysis of a tensioning process of a fine mask plate.

According to one aspect of the present invention, there is provided an analysis method of a tensioning process of a fine mask plate, including steps of: establishing a finite element model of the fine mask plate; obtaining, according to the finite element model of the fine mask plate, an optimal tensile force F1 applied to two stressed ends of the fine mask plate when the fine mask plate is in an optimal amount of deformation L1; establishing a finite element model of a metal frame for securing N fine mask plates; and obtaining, according to the optimal tensile force F1 and the finite element model of the metal frame, an actual counterforce applied to two welding sides of the metal frame before each of the fine mask plates is welded onto the metal frame.

According to an embodiment of the present invention, the step of obtaining, according to the finite element model of the fine mask plate, the optimal tensile force F1 applied to the two stressed ends of the fine mask plate when the fine mask plate is in the optimal amount of deformation L1 may include: emulating, according to the finite element model of the fine mask plate, an amount of test tensile deformation L2 of the fine mask plate when the tensile force applied to the two stressed ends of the fine mask plate is a test tensile force F2; and calculating, according to the test tensile force F2 and the amount of test tensile deformation L2, the optimal tensile force F1 applied to the two stressed ends of the fine mask plate when the fine mask plate is in the optimal amount of deformation L1, wherein $$F1 = \frac{F2 * L1}{L2}.$$

According to an embodiment of the present invention, the actual counterforce may include a left counterforce LCF, a center counterforce CCF and a right counterforce RCF, wherein the center counterforce CCF acts on a midpoint of a welding side of the metal frame, and the left counterforce LCF and the right counterforce RCF act on positions at a quarter of the welding side, respectively. The step of obtaining, according to the optimal tensile force F1 and the finite element model of the metal frame, the actual counterforce applied to the two welding sides of the metal frame before each of the fine mask plates is welded onto the metal frame may include: emulating, according to the finite element model of the metal frame, a maximum amount of deformation Lmax of the metal frame when the optimal tensile force F1 is applied to every welding point on the metal frame; obtaining, according to the finite element model of the metal frame, a reference counterforce CF when only the reference counterforce CF is applied to midpoints of the two welding sides of the metal frame and when the metal frame is in the maximum amount of deformation Lmax; obtaining, according to the reference counterforce CF, a set of a left counterforce LCF_1, a center counterforce CCF_1 and a right counterforce RCF_1 all applied to the metal frame before a first fine mask plate is welded onto the metal frame, wherein the reference counterforce CF, the left counterforce LCF_1, the center counterforce CCF_1 and the right counterforce RCF_1 meet the following conditions:

$$\begin{cases} LCF\_1 \leq CF \\ CCF\_1 \leq CF \\ RCF\_1 \leq CF \\ LCF\_1 = RCF\_1 \\ LCF\_1 + CCF\_1 + RCF\_1 \geq CF \\ 3*LCF\_1 \leq CCF\_1 \leq 4*LCF\_1 \end{cases};$$

and emulating, according to the left counterforce LCF_1, center counterforce CCF_1, the right counterforce RCF_1 and the finite element model of the metal frame, a left counterforce, a center counterforce and a right counterforce applied to the metal frame before each of the remaining N−1 fine mask plates is welded onto the metal frame.

According to an embodiment of the present invention, the step of emulating, according to the left counterforce LCF_1, the center counterforce CCF_1, the right counterforce RCF_1 and the finite element model of the metal frame, the left counterforce, the center counterforce and the right counterforce applied to the metal frame before each of the remaining N−1 fine mask plates is welded onto the metal frame may include: in the finite element model of the metal frame, maintaining a left counterforce LCF_i−1, a center counterforce CCF_i−1and a right counterforce RCF_i−1 all applied to the metal frame before the (i−1)$^{th}$ fine mask plate is welded onto the metal frame and the optimal tensile force F1 applied to corresponding welding points of all the previous i-2 fine mask plates, and applying the optimal tensile force F1 to the welding points, corresponding to the (i−1)$^{th}$ fine mask plate, on the metal frame; and reducing at least one of the left counterforce LCF_i−1, the center counterforce CCF_i−1 and the right counterforce RCF_i−1until the finite element model of the metal frame is in the maximum amount of deformation Lmax, to obtain a corresponding left counterforce LCF_i, center counterforce CCF_i, and right counterforce RCF_i applied to the metal frame before the i$^{th}$ fine mask plate is welded onto the metal frame, wherein 2≤i≤N.

According to an embodiment of the present invention, in the process of reducing at least one of the left counterforce LCF_i−1, the center counterforce CCF_i−1 and the right counterforce RCF_i−1, the center counterforce CCF_i−1 may be reduced first, and then the left counterforce LCF_i−1 and/or the right counterforce RCF_i−1 may be reduced.

According to an embodiment of the present invention, the step of obtaining, according to the finite element model of the metal frame, the reference counterforce CF when only the reference counterforce CF is applied to the midpoints of the two welding sides of the metal frame and when the metal frame is in the maximum amount of deformation Lmax may include: emulating, according to the finite element model of the metal frame, an amount of test compressive deformation TL of the metal frame when a test counterforce TCF is applied only to the midpoints of the two welding sides of the metal frame; and calculating, according to the test counterforce TCF and the amount of test compressive deformation TL, the reference counterforce CF applied to the midpoints of the two welding sides of the metal frame when the metal frame is in the maximum amount of deformation Lmax, wherein $$CF = \frac{TCF * L\max}{TL}.$$

According to an embodiment of the present invention, the finite element model of the fine mask plate is a ¼ model of the fine mask plate.

The present invention has the following beneficial effects:

The present invention provides an analysis method of a tensioning process of a fine mask plate. The analysis method, based on the simulation function of ANSYS software, finds an appropriate tensile force for stretching a fine mask plate and a corresponding actual counterforce applied to a metal frame before each fine mask plate is welded onto the metal frame through establishing a finite element model of the fine mask plate and a finite element model of the metal frame. The analysis process requires no physical tests, thereby effectively avoiding damaging the fine mask plate and further effectively saving the test cost.

DESCRIPTION OF THE PREFERRED EMBODIMENT

In order to make those skilled in the art understand the technical solution of the present invention better, an analysis method of a tensioning process of a fine mask plate provided by the present invention will be described below in detail with reference to the accompanying drawings.

Figure 1:
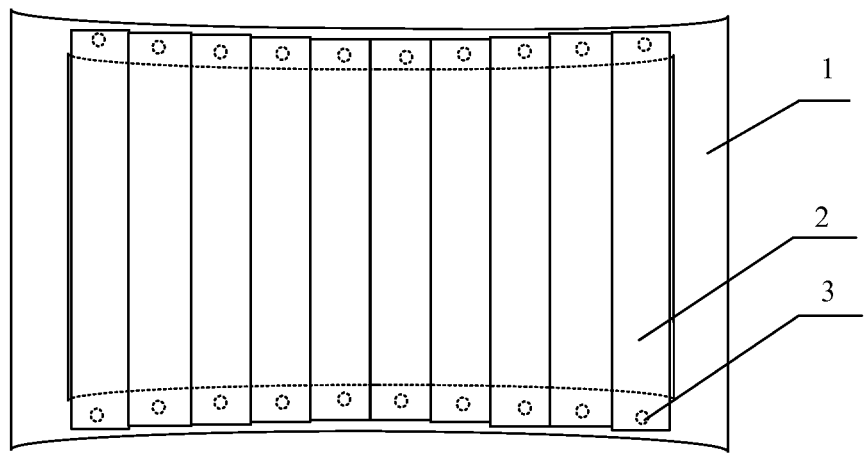
FIG. 1 is a schematic diagram illustrating a case where a plurality of fine mask plates are welded to a metal frame.
Figure 2:
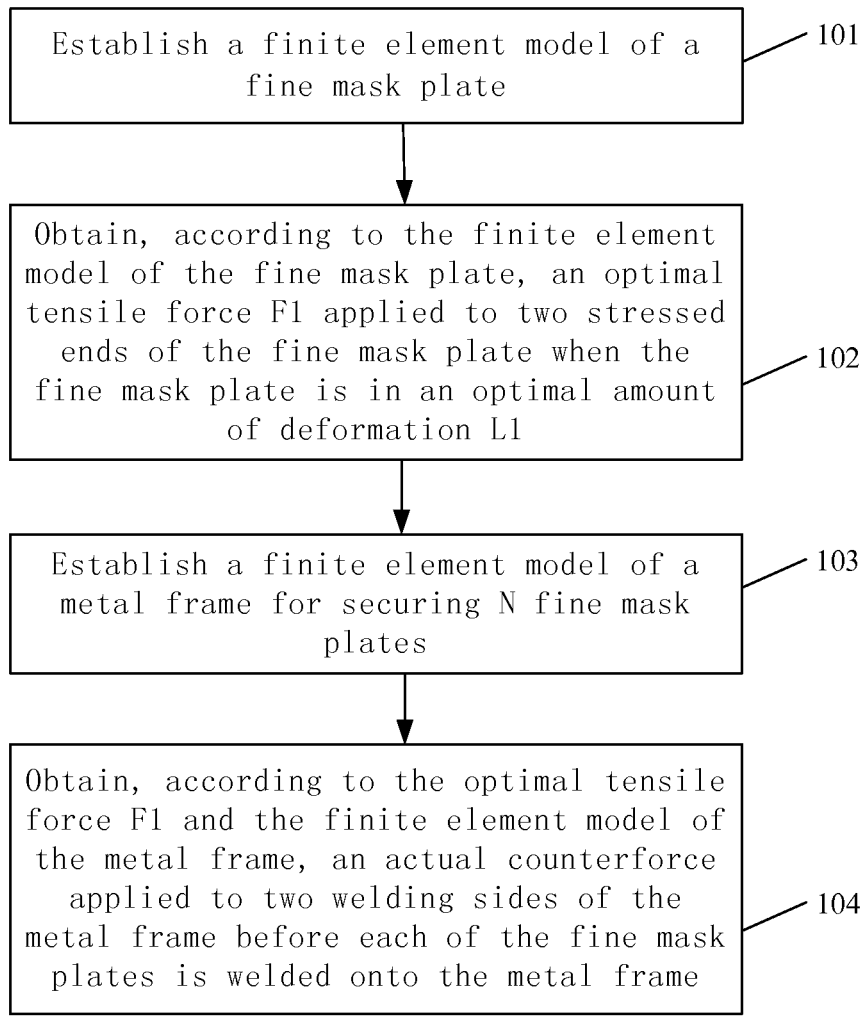
FIG. 2 is a flowchart of an analysis method of a tensioning process of a fine mask plate provided by an embodiment of the present invention.

FIG. 2 is a flowchart of an analysis method of a tensioning process of a fine mask plate provided by an embodiment of the present invention. As shown in FIG. 2, the analysis method includes:

Step 101: A finite element model of a fine mask plate is established.

In step 101, a corresponding APDL command stream is written according to the specification and dimension of the fine mask plate and this APDL command stream is run in ANSYS software to establish a finite element model of a fine mask plate. Specifically, based on the symmetry of the fine mask plate and the computation speed of the ANSYS system, a ¼ model of the fine mask plate may be established through a pre-processing module in the ANSYS system and then mesh-divided, and corresponding boundary conditions are applied.

Step 102: According to the finite element model of the fine mask plate, an optimal tensile force F1 applied to two stressed ends of the fine mask plate when the fine mask plate is in an optimal amount of deformation L1 is obtained.

Step 102 includes:

Step 1021: According to the finite element model of the fine mask plate, an amount of test tensile deformation L2 of the fine mask plate when the tensile force applied to the two stressed ends of the fine mask plate is a test tensile force F2 is emulated.

Figure 3:
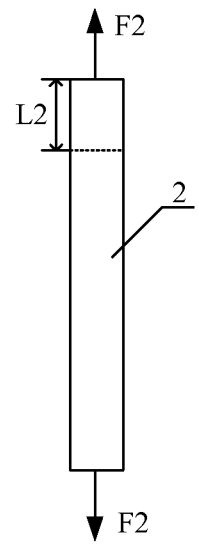
FIG. 3 is a schematic diagram corresponding to step 1021 in the embodiment of the present invention.

FIG. 3 is a schematic diagram corresponding to step 1021 in the embodiment of the present invention. As shown in FIG. 3, in step 1021, first, the test tensile force F2 is applied to the finite element model of the fine mask plate 2, and calculation is performed by a solver in the ANSYS software. Then, after the emulation process is finished, the test tensile deformation L2 of the finite element model of the fine mask plate 2 is obtained from a post-processing module of the ANSYS software.

Step 1022: According to the test tensile force F2 and the amount of test tensile deformation L2, the optimal tensile force F1 applied to the two stressed ends of the fine mask plate when the fine mask plate is in the optimal amount of deformation L1 is calculated, wherein $$F1 = \frac{F2 * L1}{L2}.$$

In step 1022, first, from preliminary experimental tests, it may be known that an amount of deformation of the fine mask plate during the evaporation process is the optimal amount of deformation L1. Then, based on the principle that the elastic modulus of the fine mask plate is constant, it can be concluded that $$\frac{F1}{L1} = \frac{F2}{L2},$$

based on which, it can be concluded that $$F1 = \frac{F2 * L1}{L2}.$$

Step 103: A finite element model of a metal frame for securing N fine mask plates is established.

In step 103, a corresponding APDL command stream is written according to the specification and dimension of the metal frame and this APDL command stream is run in the ANSYS software to establish a finite element model of the metal frame; and this finite element model is then mesh-divided, and corresponding boundary conditions are applied.

Step 104: According to the optimal tensile force F1 and the finite element model of the metal frame, an actual counterforce applied to two welding sides of the metal frame before each of the fine mask plates is welded onto the metal frame is obtained.

Step 104 includes:

Step 1041: According to the finite element model of the metal frame, a maximum amount of deformation Lmax of the metal frame when the optimal tensile force F1 is applied to every welding point on the metal frame is emulated.

Figure 4:
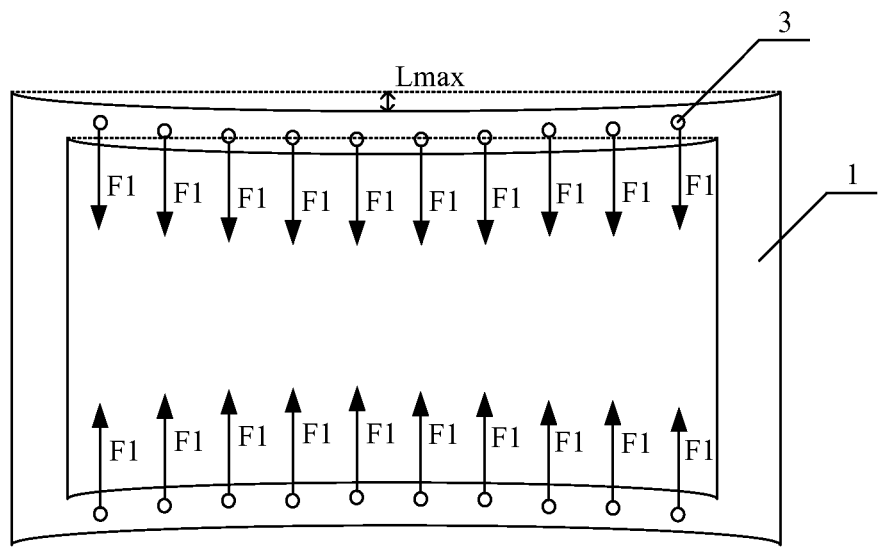
FIG. 4 is a schematic diagram corresponding to step 1041 in the embodiment of the present invention.

FIG. 4 is a schematic diagram corresponding to step 1041 in the embodiment of the present invention. As shown in FIG. 4, in step 1041, first, the optimal tensile force F1 is applied to every corresponding welding point 3 in the finite element model of the metal frame 1 and calculation is performed by a solver in the ANSYS software. Then, after emulation process is finished, the maximum amount of deformation Lmax of the finite element model of the metal frame 1 is obtained from a post-processing module of the ANSYS software. It needs to be noted that this process is used for emulating the deformation of the metal frame when all of the N fine mask plates are welded onto the metal frame.

Step 1042: According to the finite element model of the metal frame, a reference counterforce CF when the reference counterforce CF is applied only to the midpoints of two welding sides of the metal frame and the metal frame is in the maximum amount of deformation Lmax is obtained.

Figure 5:
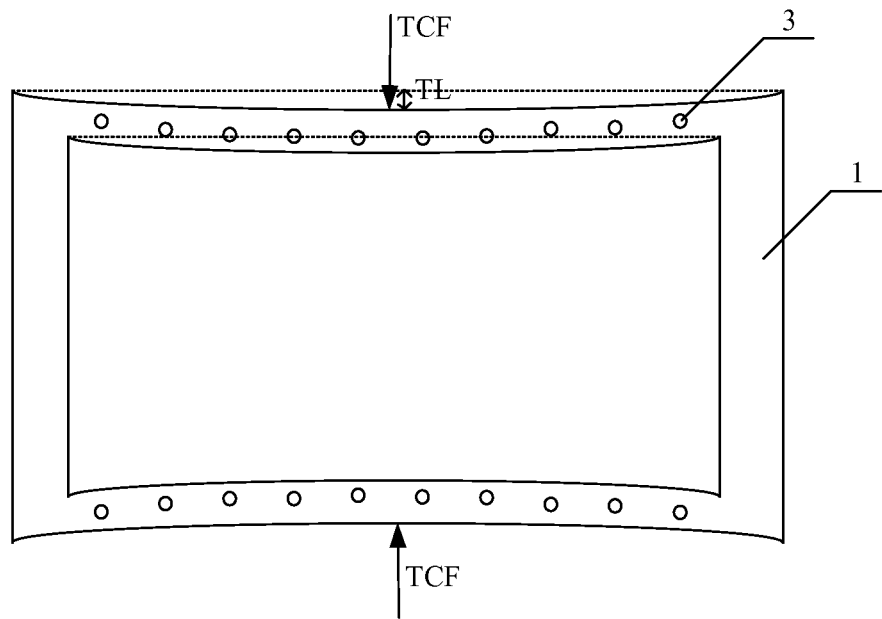
FIG. 5 is a schematic diagram corresponding to step 10421 in the embodiment of the present invention.

Optionally, step 1042 includes:

Step 10421: According to the finite element model of the metal frame, an amount of test compressive deformation TL of the metal frame when a test counterforce TCF is applied only to the midpoints of the two welding sides of the metal frame is emulated;

FIG. 5 is a schematic diagram corresponding to step 10421 in the embodiment of the present invention. As shown in FIG. 5, in step 10421, the amount of test compressive deformation TL of the finite element model of the metal frame 1 when the test counterforce TCF is applied only to the midpoints of the two welding sides of the finite element model of the metal frame 1 is emulated. The emulation process for obtaining the test compressive deformation TL is similar to that for obtaining the maximum amount of deformation Lmax, and is not repeated redundantly here.

Step 10422: According to the test counterforce TCF and the amount of test compressive deformation TL, the reference counterforce CF applied to the midpoints of the two welding sides of the metal frame when the metal frame is in the maximum amount of deformation Lmax is calculated, wherein $$CF = \frac{TCF * L\max}{TL}.$$

In step 10422, based on the principle that the elastic modulus of the metal frame is constant, it can be concluded that $$\frac{CF}{L\max} = \frac{TCF}{TL},$$

based on which, it can be concluded that $$CF = \frac{TCF * L\max}{TL}.$$

Step 1043: According to the reference counterforce CF, a set of a left counterforce LCF_1, a center counterforce CCF_1 and a right counterforce RCF_1 all applied to the metal frame before a first fine mask plate is welded onto the metal frame is obtained, wherein the reference counterforce CF, the left counterforce LCF_1, the center counterforce CCF_1 and the right counterforce RCF_1 meet the following conditions:

$$\begin{cases} LCF\_1 \leq CF \\ CCF\_1 \leq CF \\ RCF\_1 \leq CF \\ LCF\_1 = RCF\_1 \\ LCF\_1 + CCF\_1 + RCF\_1 \geq CF \\ 3*LCF\_1 \leq CCF\_1 \leq 4*LCF\_1 \end{cases}$$

Figure 6:
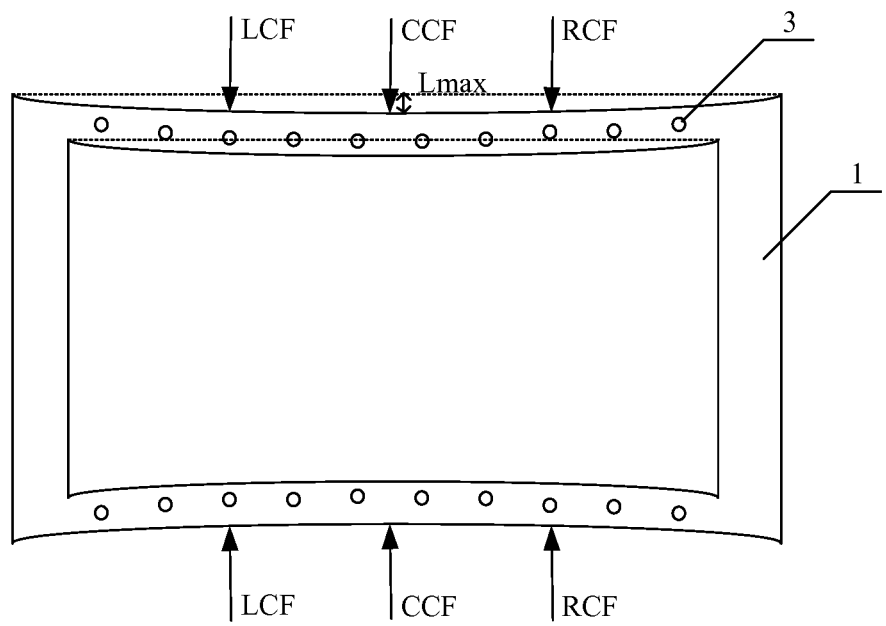
FIG. 6 is a schematic diagram corresponding to step 1043 in the embodiment of the present invention.

FIG. 6 is a schematic diagram corresponding to step 1043 in the embodiment of the present invention. As shown in FIG. 6, in order to ensure the uniformity of deformation of the metal frame, for the existing tensioning equipment, the application of one force to a midpoint of the welding side of the metal frame 1 is replaced by application of three forces respectively to three points of the welding side (i.e., an actual counter force); and the three forces are a left counterforce LCF, a center counterforce CCF and a right counterforce RCF, respectively, wherein the center counterforce CCF acts on the midpoint of the welding side of the metal frame 1, and the left counterforce LCF and the right counterforce RCF act on positions at a quarter of the welding side of the metal frame 1, respectively.

In this embodiment, the reference counterforce CF, the left counterforce LCF_1, the center counterforce CCF_1 and the right counterforce RCF_1 meet the following conditions:

the left counterforce LCF_1, the center counterforce CCF_1 and the right counterforce RCF_1 are all smaller than the reference counterforce CF, i.e., LCF_1≤CF, CCF_1≤CF, and RCF_1≤CF.

In addition, in order to ensure that the metal frame 1 is stressed uniformly, before a first mask plate is welded onto the metal frame 1, the left counterforce LCF_1 is equal to the right counterforce RCF_1, i.e., LCF_1=RCF_1.

Meanwhile, the sum of the left counterforce LCF_1, the center counterforce CCF_1 and the right counterforce RCF_1 is greater than the reference counterforce CF, i.e., LCF_1+CCF_1+RCF_1≥CF.

Finally, the center counterforce CCF_1 is three to four times the value of the left counterforce LCF_1 (or the right counterforce RCF_1), i.e., 3*LCF_1≤CCF_1≤4* LCF_1.

When all the above conditions are met, numerous groups of solutions may be obtained according to the reference counterforce CF. In this embodiment, it only needs to pick any one group of solutions among the numerous groups of solutions for emulating.

With the above step 1041 and step 1042, a set of a left counterforce LCF_1, a center counterforce CCF_1 and a right counterforce RCF_1 applied to the metal frame 1 before the first fine mask plate is welded onto the metal frame 1 can be emulated.

Step 1044: According to the left counterforce LCF_1, the center counterforce CCF_1, the right counterforce RCF_1 and the finite element model of the metal frame, a left counterforce, a center counterforce and a right counterforce applied to the metal frame before each of the remaining N−1 fine mask plates is welded onto the metal frame are emulated.

Step 1044 includes;

Step 10441: In the finite element model of the metal frame, a left counterforce LCF_i−1, a center counterforce CCF_i−1, a right counterforce RCF_i−1 applied to the metal frame before the (i−1)$^{th}$ fine mask plate is welded onto the metal frame and a corresponding optimal tensile force F1 applied to welding points of all the previous i-2 fine mask plates are maintained, and the optimal tensile force F1 is applied to welding points, corresponding to the (i−1)$^{th}$ fine mask plate, on the metal frame.

Step 10442: At least one of the left counterforce LCF_i−1, the center counterforce CCF_i−1 and the right counterforce RCF_i−1 is reduced until the finite element model of the metal frame is in the maximum amount of deformation Lmax, to obtain a left counterforce LCF_i, a center counterforce CCF_i, and a right counterforce RCF_i applied to the metal frame before the i$^{th}$ fine mask plate is welded onto the metal frame, wherein 2≤i≤N.

Taking that a left counterforce, a center counterforce and a right counterforce applied to the metal frame before a second and a third fine mask plate are welded onto the metal frame are emulated as an example, step 10441 and step 10442 will be described below in detail with reference to the accompanying drawings.

Figure 7:
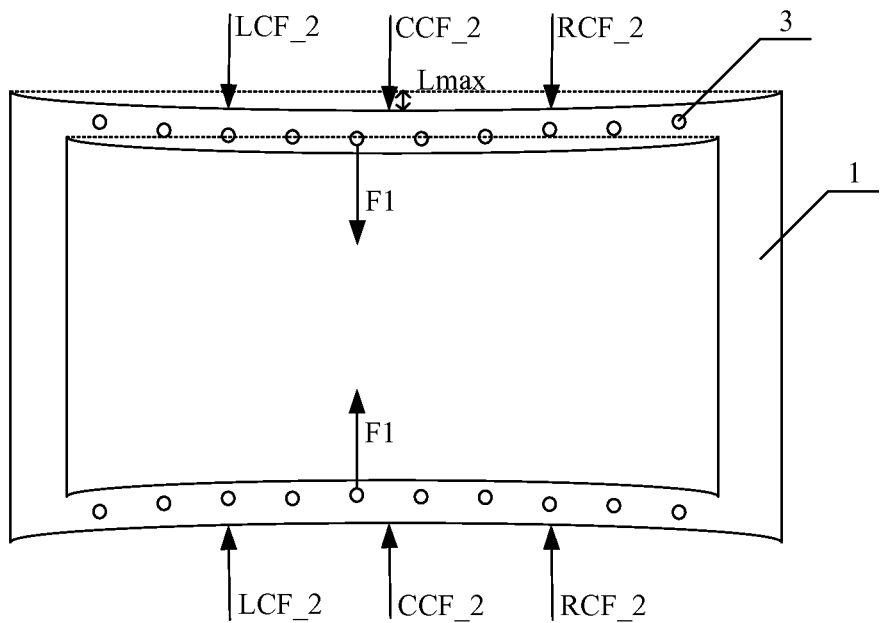
FIG. 7 is a schematic diagram of emulating stress condition of a finite element model of a metal frame before a second fine mask plate is welded onto the metal frame.

FIG. 7 is a schematic diagram of emulating stress condition of a finite element model of a metal frame before a second fine mask plate is welded onto the metal frame. As shown in FIG. 7, first, in the finite element model of the metal frame 1, the left counterforce LCF_1, the center counterforce CCF_1 and the right counterforce RCF_1 applied to the metal frame 1 before the first fine mask plate is welded onto the metal frame 1 are maintained, and the optimal tensile force F1 is applied to the welding points 3, corresponding the first fine mask plate, on the metal frame 1 (in order to emulate a case where the first fine mask plate has been welded onto the metal frame). At this moment, the amount of deformation of the finite element model of the metal frame 1 is inevitably greater than the maximum amount of deformation Lmax. Then, at least one of the left counterforce LCF_1, the center counterforce CCF_1 and the right counterforce RCF_1 is reduced until the finite element model of the metal frame 1 gets back to the maximum amount of deformation Lmax. At this moment, it can be known from the ANSYS software that the current three counterforces are a left counterforce LCF_2, a center counterforce CCF_2 and a right counterforce RCF_2, respectively. That is, a corresponding left counterforce LCF_2, a center counterforce CCF_2 and a right counterforce RCF_2, applied to the metal frame 1 before the second fine mask plate is welded onto the metal frame 1, are emulated.

The process for emulating the left counterforce, the center counterforce and the right counterforce applied to the metal frame 1 before the second fine mask plate is welded onto the metal frame 1 is finished.

Figure 8:
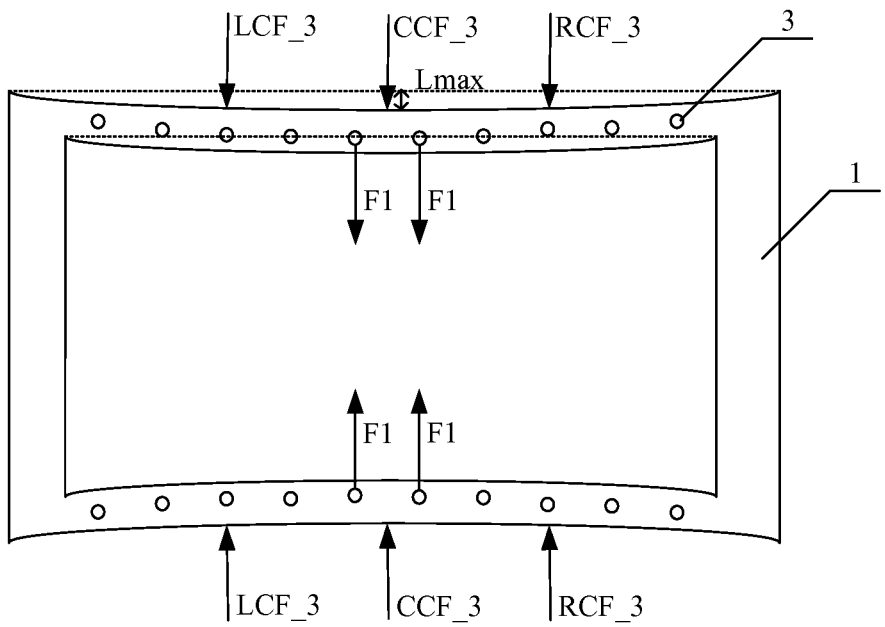
FIG. 8 is a schematic diagram of emulating stress condition of a finite element model of a metal frame before a third fine mask plate is welded onto the metal frame.

FIG. 8 is a schematic diagram of emulating stress condition of a finite element model of a metal frame before a third fine mask plate is welded onto the metal frame. As shown in FIG. 8, first, in the finite element model of the metal frame 1, the left counterforce LCF_2, the center counterforce CCF_2 and the right counterforce RCF_2 applied to the metal frame 1 before the second fine mask plate is welded onto the metal frame 1 are maintained; the optimal tensile force F1 applied to the welding points 3 corresponding to the first fine mask plate is maintained (in order to emulate a case where the first fine mask plate has been welded onto the metal frame); and the optimal tensile force F1 is applied to the welding points 3, corresponding to the second fine mask plate, on the metal frame 1 (in order to emulate a case where the second fine mask plate has been welded onto the metal frame). At this moment, the amount of deformation of the finite element model of the metal frame 1 is inevitably greater than the maximum amount of deformation Lmax. Then, at least one of the left counterforce LCF_2, the center counterforce CCF_2 and the right counterforce RCF_2 is reduced until the finite element model of the metal frame 1 gets back to the maximum amount of deformation Lmax. At this moment, it can be known from the ANSYS software that the current three counterforces are a left counterforce LCF_3, a center counterforce CCF_3 and a right counterforce RCF_3, respectively. That is, a corresponding left counterforce LCF_3, a center counterforce CCF_3 and a right counterforce RCF_3, applied to the metal frame 1 before the third fine mask plate is welded onto the metal frame 1, are emulated.

The process for emulating the left counterforce, the center counterforce and the right counterforce applied to the metal frame 1 before the third fine mask plate is welded onto the metal frame 1 is finished.

The above emulation process is repeated until a corresponding left counterforce LCF_N, a center counterforce CCF_N and a right counterforce RCF_N, applied to the metal frame 1 before the N$^{th}$ fine mask plate is welded onto the metal frame 1, are obtained.

It should be noted that in the above emulation process, when the fine mask plates are welded one by one, symmetrically welding from the middle of the metal frame 1 to both sides thereof is usually employed. Hence, in emulating a left counterforce, a center counterforce and a right counterforce applied to the metal frame 1 before each of the remaining N−1 fine mask plates is welded onto the metal frame 1, the center counterforce CCF is usually reduced first, then the left counterforce LCF and/or the right counterforce RCF are/is reduced. When the optimal tensile force F1 is applied to every corresponding welding point 3 in the finite element model of the metal frame 1 (a case where all the N fine mask plates have been welded onto the metal frame is emulated), and the left counterforce, the center counterforce and the right counterforce all have a value of 0, the finite element model of the metal frame 1 is in the maximum amount of deformation Lmax. The entire emulation process is finished, and N groups of different actual counterforces (including: the left counterforces, the center counterforces and the right counterforces) may be obtained through the above emulation process.

In order to show a continuous tensioning process better, the finite element model of the fine mask plate, the finite element model of the metal frame and the actual counterforce applied to the metal frame before each of the fine mask plates obtained in the above step 104 is melded onto the metal frame, may be all input into the ANSYS software through an APDL command stream, in order to emulate the welding process of each of the fine mask plates.

The embodiment of the present invention provides an analysis method of a tensioning process of a fine mask plate. The analysis method, based on the simulation function of the ANSYS software, finds an appropriate tensile force for stretching a fine mask plate and a corresponding actual counterforce applied to a metal frame before each fine mask plate is welded onto the metal frame through establishing a finite element model of the fine mask plate and a finite element model of the metal frame. The analysis process requires no physical tests, thereby effectively avoiding damaging the fine mask plate and further effectively saving the test cost.

It may be understood that, the above implementations are exemplary implementations merely used to describe the principle of the present invention, and the present invention is not limited thereto. For a person of ordinary skill in the art, various variations and improvements may be made without departing from the spirit and essence of the present invention, and those variations and improvements should also be regarded as falling into the protection scope of the present invention.

The invention claimed is:

1. An analysis method of a tensioning process of a fine mask plate, comprising steps of:
establishing a finite element model of the fine mask plate;
obtaining, according to the finite element model of the fine mask plate, an optimal tensile force F1 applied to two stressed ends of the fine mask plate when the fine mask plate is in an optimal amount of deformation L1;
establishing a finite element model of a metal frame for securing N fine mask plates; and
obtaining, according to the optimal tensile force F1 and the finite element model of the metal frame, an actual counterforce applied to two welding sides of the metal frame before each of the fine mask plates is welded onto the metal frame,
wherein the actual counterforce comprises a left counterforce LCF, a center counterforce CCF and a right counterforce RCF, and
the step of obtaining, according to the optimal tensile force F1 and the finite element model of the metal frame, the actual counterforce applied to the two welding sides of the metal frame before each of the fine mask plates is welded onto the metal frame comprises:
emulating, according to the finite element model of the metal frame, a maximum amount of deformation Lmax of the metal frame when the optimal tensile force F1 is applied to every welding point on the metal frame, the deformation Lmax being directed to an inside of the metal frame;
obtaining, according to the finite element model of the metal frame, a reference counterforce CF when only the reference counterforce CF is applied to the midpoints of the two welding sides of the metal frame and when the metal frame is in the maximum amount of deformation Lmax;
obtaining, according to the reference counterforce CF, a set of a left counterforce LCF_1, a center counterforce CCF_1 and a right counterforce RCF_1 all applied to the metal frame before a first fine mask plate is welded onto the metal frame, wherein the reference counterforce CF, the left counterforce LCF_1, the center counterforce CCF_1 and the right counterforce RCF_1 meet the following conditions:

$$\begin{cases} LCF\_1 \le CF \\ CCF\_1 \le CF \\ RCF\_1 \le CF \\ LCF\_1 = RCF\_1 \\ LCF\_1 + CCF\_1 + RCF\_1 \ge CF \\ 3*LCF\_1 \le CCF\_1 \le 4*LCF\_1 \end{cases};$$

and
emulating, according to the left counterforce LCF_1, the center counterforce CCF_1, the right counterforce RCF_1 and the finite element model of the metal frame, a left counterforce, a center counterforce and a right counterforce applied to the metal frame before each of the remaining N−1 fine mask plates is welded onto the metal frame.

2. The analysis method of a tensioning process of a fine mask plate according to claim 1, wherein the step of obtaining, according to the finite element model of the fine mask plate, the optimal tensile force F1 applied to the two stressed ends of the fine mask plate when the fine mask plate is in the optimal amount of deformation L1 comprises:
emulating, according to the finite element model of the fine mask plate, an amount of test tensile deformation L2 of the fine mask plate when the tensile force applied to the two stressed ends of the fine mask plate is a test tensile force F2; and
calculating, according to the test tensile force F2 and the amount of test tensile deformation L2, the optimal tensile force F1 applied to the two stressed ends of the fine mask plate when the fine mask plate is in the optimal amount of deformation L1, wherein $$F1 = \frac{F2*L1}{L2}.$$

3. The analysis method of a tensioning process of a fine mask plate according to claim 1, wherein the center counterforce CCF acts on a midpoint of a welding side of the metal frame, and the left counterforce LCF and the right counterforce RCF act on positions at a quarter of the welding side, respectively.

4. The analysis method of a tensioning process of a fine mask plate according to claim 3, wherein the step of emulating, according to the left counterforce LCF_1, the center counterforce CCF_1, the right counterforce RCF_1 and the finite element model of the metal frame, the left counterforce, the center counterforce and the right counterforce applied to the metal frame before each of the remaining N−1 fine mask plates is welded onto the metal frame comprises:

in the finite element model of the metal frame, maintaining a left counterforce LCF_i−1, a center counterforce CCF_i−1 and a right counterforce RCF_i−1 all applied to the metal frame before the (i−1)th fine mask plate is welded onto the metal frame and the optimal tensile force F1 applied to corresponding welding points of all the previous i-2 fine mask plates, and applying the optimal tensile force F1 to the welding points, corresponding to the (i−1)th fine mask plate, on the metal frame; and reducing at least one of the left counterforce LCF_i−1, the center counterforce CCF_i−1and the right counterforce RCF_i−1 until the finite element model of the metal frame is in the maximum amount of deformation Lmax, to obtain a left counterforce LCF_i, a center counterforce CCF_i, and a right counterforce RCF_i applied to the metal frame before the i th fine mask plate is welded onto the metal frame, wherein 2≤i≤N.

5. The analysis method of a tensioning process of a fine mask plate according to claim 4, wherein in the process of reducing at least one of the left counterforce LCF_i−1, the center counterforce CCF_i−1 and the right counterforce RCF_i−1, the center counterforce CCF _i−1 is reduced first, then the left counterforce LCF_i−1 and/or the right counterforce RCF_i−1 are/is reduced.

6. The analysis method of a tensioning process of a fine mask plate according to claim 3, wherein the step of obtaining, according to the finite element model of the metal frame, the reference counterforce CF when only the reference counterforce CF is applied to the midpoints of the two welding sides of the metal frame and when the metal frame is in the maximum amount of deformation Lmax comprises:

emulating, according to the finite element model of the metal frame, an amount of test compressive deformation TL of the metal frame when a test counterforce TCF is applied to the two welding sides of the metal frame; and calculating, according to the test counterforce TCF and the amount of test compressive deformation TL, the reference counterforce CF applied to the two welding sides of the metal frame when the metal frame is in the maximum amount of deformation Lmax, wherein $$CF = \frac{TCF * L\max}{TL}.$$

7. The analysis method of a tensioning process of a fine mask plate according to claim 1, wherein the finite element model of the fine mask plate is a ¼ model of the fine mask plate.

* * * * *